United States Patent
Sperry et al.

(10) Patent No.: US 10,980,554 B2
(45) Date of Patent: Apr. 20, 2021

(54) RETRIEVAL SYSTEM

(71) Applicant: Boston Scientific Scimed, Inc., Maple Grove, MN (US)

(72) Inventors: Erik Sperry, Newburyport, MA (US);
Ronald Ciulla, Westford, MA (US);
Aaron Kirkeom, Gladstone, NJ (US);
Mark Hera, Holden, MA (US);
Sebastian Koerner, Berlin (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/410,819

(22) Filed: Jan. 20, 2017

(65) Prior Publication Data

US 2017/0209162 A1    Jul. 27, 2017

Related U.S. Application Data

(60) Provisional application No. 62/281,930, filed on Jan. 22, 2016.

(51) Int. Cl.
*A61B 17/221* (2006.01)
*A61B 17/22* (2006.01)
(Continued)

(52) U.S. Cl.
CPC ...... *A61B 17/221* (2013.01); *A61B 17/00234* (2013.01); *A61B 17/320758* (2013.01);
(Continued)

(58) Field of Classification Search
CPC ............ A61B 17/00234; A61B 17/221; A61B 2017/00358; A61B 2017/22044; A61B 2017/003; A61B 2017/00477; A61B 2017/22072; A61B 2017/22079; A61B 2017/22082; A61B 2017/2212; A61B 17/320758; A61B 2017/320775;
(Continued)

(56) References Cited

U.S. PATENT DOCUMENTS 6,068,645 A  5/2000  Tu
7,771,435 B2  8/2010  Poll
(Continued)

FOREIGN PATENT DOCUMENTS

CN  104068910 A  10/2014
JP  2003503142 A  1/2003
JP  2010524651 A  7/2010

OTHER PUBLICATIONS

International Search Report and Written Opinion dated Mar. 30, 2017, for PCT/US2017/014214 (10 pages).

*Primary Examiner* — George J Ulsh
*Assistant Examiner* — Andrew P. Restaino
(74) *Attorney, Agent, or Firm* — Kacvinsky Daisak Bluni PLLC

(57) ABSTRACT

This disclosure concerns systems and methods for removal of material from the body of a patient, and particularly for percutaneous nephrolithotomy. Systems according to the various embodiments of the disclosure include one or more of nested first and second components, for instance a scope nested within a suction or irrigation catheter, guidewires with self-expanding distal tips, and wash-out elements to facilitate rapid removal of stones through an access sheath.

5 Claims, 2 Drawing Sheets

(51) Int. Cl.
*A61B 17/00* (2006.01)
*A61B 17/3207* (2006.01)
*A61B 17/34* (2006.01)

(52) U.S. Cl.
CPC ..... *A61B 17/3421* (2013.01); *A61B 2017/003* (2013.01); *A61B 2017/00296* (2013.01); *A61B 2017/00358* (2013.01); *A61B 2017/00477* (2013.01); *A61B 2017/2212* (2013.01); *A61B 2017/22044* (2013.01); *A61B 2017/22072* (2013.01); *A61B 2017/22079* (2013.01); *A61B 2017/22082* (2013.01); *A61B 2017/320775* (2013.01); *A61B 2217/007* (2013.01)

(58) Field of Classification Search
CPC ......... A61B 17/3421; A61B 2217/007; A61M 2025/09175
USPC ........................................................ 606/128
See application file for complete search history.

(56) References Cited

U.S. PATENT DOCUMENTS

| | | | |
|---|---|---|---|
| 2003/0176769 | A1* | 9/2003 | Soble .................... A61B 1/005 600/114 |
| 2005/0261705 | A1 | 11/2005 | Gist |
| 2008/0255596 | A1* | 10/2008 | Jenson ................ A61B 17/221 606/159 |
| 2009/0270808 | A1 | 10/2009 | Mas et al. |
| 2011/0245841 | A1* | 10/2011 | Shohat ................... A61B 17/22 606/127 |
| 2014/0309655 | A1* | 10/2014 | Gal ...................... A61B 17/221 606/127 |
| 2015/0025555 | A1* | 1/2015 | Sos .................... A61B 17/3207 606/159 |
| 2015/0305757 | A1* | 10/2015 | Brayman ............. A61B 17/221 606/128 |
| 2015/0359548 | A1* | 12/2015 | Dhindsa ............... A61B 17/221 606/127 |

* cited by examiner

RETRIEVAL SYSTEM

CROSS-REFERENCE TO RELATED APPLICATIONS

This application claims the benefit of priority to U.S. Provisional Application Ser. No. 62/281,930, filed Jan. 22, 2016, the disclosure of which is herein incorporated by reference in its entirety.

FIELD OF THE DISCLOSURE

This application relates to the field of medical devices and medical procedures. More particularly, the application is related to devices and methods for percutaneous and endoscopic removal and/or destruction of material, foreign and natural, from the human body.

BACKGROUND

Kidney stones (also referred to as "nephrolithiasis") affects about 5% of adults in the United States, and is characterized by the formation of stone-like accretions (or "calculi") comprising insoluble or poorly soluble excreted salts. Kidney stones, which may migrate throughout the urinary tract, can cause significant pain, and may obstruct the flow of urine or act as a nidus for infection, both of which can in turn acutely or chronically damage the kidneys.

Kidney stones are generally treated non-invasively in one of two ways, depending on stone size and position: fragmentation (lithotripsy), by means of a flexible ureteroscope or by external application of shock waves to the affected kidney, or removal (nephrolithotomy), typically by means of a percutaneously inserted cannula or needle. In a typical percutaneous nephrolithotomy (PCNL) procedure, a user identifies a stone within the renal pelvis (especially at or near the upper pole) and inserts a cannula or needle/sheath introducer apparatus through the skin and the renal cortex into the renal pelvis; the needle is then removed, leaving the sheath in place to define a channel through which the stone(s) or fragments thereof can be removed, and into which instruments can be inserted to provide irrigation and/or suction, or to manipulate the stone. The size of the sheath limits the number of instruments that can be inserted into the kidney, their size, and the size of the stone or stone fragments that can be removed is limited by the internal diameter of the sheath, and a larger sheath would be desirable to permit insertion of more and larger instruments, and removal or larger stones and/or fragments. At the same time, because insertion of the sheath through the renal cortex may damage renal function, it is desirable to minimize the size of the sheath and to maximize the utility of the devices that can be inserted therethrough. It should be noted as well that, while PCNL procedures were developed in the 1970s, these competing demands have never been fully reconciled.

SUMMARY OF THE DISCLOSURE

The present disclosure, in its various aspects, provides improved systems and methods for PCNL that permit the rapid exchange and simultaneous use of instruments.

In one aspect, the present disclosure relates to a system for removing an object from a body, which includes a catheter having a Y-connector with a first port connectable to a source of suction or irrigation and a second port sized to permit insertion of a medical device, a nephroscope at least partially insertable into the catheter through the second port, and a guidewire insertable through a working channel of the nephroscope, which guidewire includes a self-expanding element at or near its distal end. In various embodiments, the nephroscope is attached to an inner wall of the catheter, the catheter has a distal portion that expands or is expandable, and/or the catheter includes a segment configured for rapid stone exchange (i.e. to permit the removal of stones from the system without retracting an instrument through the full length of the catheter). The rapid exchange segment generally includes inner and outer tubular portions, each defining a lumen and having first and second apertures positioned opposite each other in a sidewall thereof, with the inner tubular portion being slidably disposed within the outer tubular portion. At least one of the first and second apertures of the outer tubular portion is fluidly connectable to a source of irrigation or suction. The system also optionally includes a snare insertable through the catheter and the inner tubular portion of the rapid-exchange segment, and in some cases the snare includes a basket portion moveable between an expanded configuration and a collapsed configuration and the inner tubular portion of the segment configured for rapid stone exchange includes a flange defining a diameter less than a diameter of the basket portion in the expanded configuration, the flange positioned so as to align the basket portion with the first and second apertures of the inner tubular portion of the segment configured for rapid stone exchange. The catheter may also include a handle with an actuator that moves the inner tubular portion relative to the outer tubular portion, which actuator is optionally a control wire. In some cases, the actuator controls the flow of irrigation or suction into the first and/or second aperture of the outer sheath. In some cases, the catheter includes a tapered portion to fit over a dilator. As for the guidewire, in some cases the self-expanding element includes a plurality of tines, and/or expands to form one of a convex (umbrella-like) and concave shape. The systems according to this aspect of the disclosure are useful in a variety of settings, including in percutaneous nephrolithotomy or, more generally, in the removal of an object from the body of a patient.

In another aspect, the present disclosure relates to a method of treating a patient which includes (i) inserting, into a renal pelvis of the patient and through an access sheath, a guidewire having a self-expanding element at or near its distal tip, then (ii) positioning the self-expanding element proximally to an object within the renal pelvis such that the self-expanding element assumes an expanded configuration, (iii) passing a burring instrument over the guidewire so as to contact the object, and (iv) activating the burring instrument, thereby altering a size or shape of the object. In some cases, at least one of the guidewire and the burring instrument is advanced through a working channel of a nephroscope, and at least a portion of the nephroscope is positioned within a catheter configured to apply suction or deliver fluid (e. g. the nephroscope is attached to a wall of the catheter configured to apply suction). In certain cases, the step of positioning the self-expanding element proximally to the object includes moving the object, and/or the step of activating the burring instrument includes fragmenting the object. Alternatively or additionally, the method may include inserting a snare into the renal pelvis, grasping a fragment of the object with the snare, and retracting the snare through the access sheath and engaging a stone retrieval apparatus disposed in a portion of the access sheath.

In yet another aspect, the present disclosure relates to an access sheath comprising a segment configured for rapid stone exchange which includes inner and outer tubular portions, each defining a lumen and having first and second apertures positioned opposite each other in a sidewall thereof, the inner tubular portion being slidably disposed within the outer tubular portion. At least one of the first and second apertures of the outer tubular portion is fluidly connectable to a source of irrigation or suction. The inner tubular portion is optionally sized to permit insertion of a snare having a collapsible basket, in which case it is also optionally built to include a flange defining a diameter less than a diameter of the basket of the snare in an expanded configuration, the flange positioned so as to align the basket portion with the first and second apertures of the inner tubular portion. Alternatively or additionally, the access sheath includes a handle having an actuator configured to move the inner tubular portion relative to the outer tubular portion, which actuator is optionally a control wire and/or is configured to control a source of irrigation or suction fluidly connected to one of the first and second apertures of the outer tubular portion. In some cases, the access sheath includes a tapered portion to fit over a dilator.

DRAWINGS

Aspects of the disclosure are described below with reference to the following drawings in which like numerals reference like elements, and wherein.

Unless otherwise provided in the following specification, the drawings are not necessarily to scale, with emphasis being placed on illustration of the principles of the disclosure.

DETAILED DESCRIPTION OF THE PREFERRED EMBODIMENTS

Figure 1:
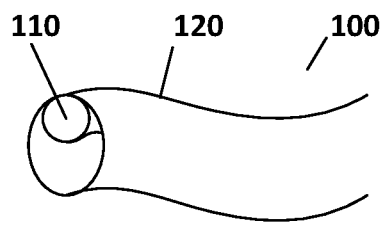
FIG. 1 shows a schematic view of a distal portion of a nephrolithotomy system in which a scope or other device is fixedly attached to, and disposed within the lumen of, a suction tube
Figure 2:
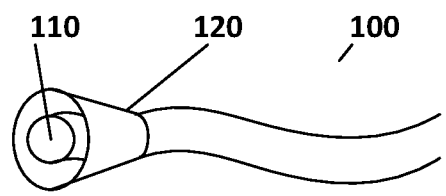
FIG. 2 shows a schematic view of a distal portion of a nephrolithotomy system in which a scope or other device is disposed within the lumen of an expandable suction tube.
Figure 4:
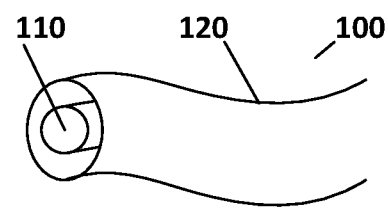
FIG. 4 shows a schematic view of a distal portion of a nephrolithotomy system in which a scope or other device is disposed within the lumen of an expandable suction tube.
Figure 5A:
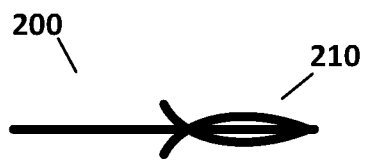
FIGS. 5A and 5B show an exemplary guidewire having an expandable tip in collapsed (5A) and expanded (5B) configurations.
Figure 6A:
FIGS. 6A and 6B show an exemplary guidewire having an expandable tip in collapsed (6A) and expanded (6B) configurations.
Figure 5B:
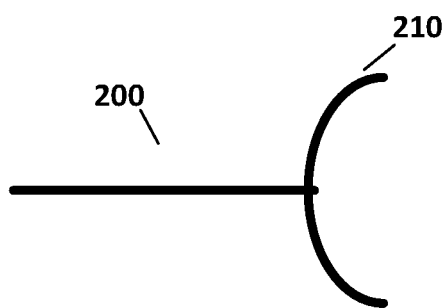
Figure 6B:
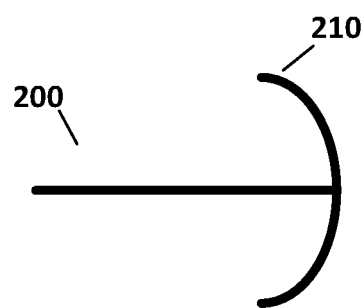

In general, the various systems and methods of the present disclosure make more efficient use of PCNL sheaths by facilitating rapid instrument exchange and/or side-by-side or piggyback deployment of multiple instruments through a single PCNL sheath. Turning first to FIGS. 1, 2 and 4, some systems 100 according to the present disclosure nest instruments one inside the other, particularly nesting a scope or catheter 110 defining a lumen within a body of tubing 120 for providing suction and/or irrigation. The scope or catheter 110 is optionally fixedly attached to an interior (FIG. 1) or exterior (not shown) wall of the tubing 120, though it may be unattached and freely-disposed within the tubing 120 as shown in FIGS. 2 and 4. The tubing 120 is preferably configured to be (e.g., it incorporates a polymer material having sufficient elasticity or flexibility and has a wall thickness that permits it to be) threaded through tortuous anatomy and/or bent through relatively small diameter arcs. In some cases, a portion of the tubing 120 is collapsible and/or expandable, so it can decrease in diameter when passed through a PCNL sheath and/or increase in diameter once passed into the renal pelvis or another body lumen. In some instances, such as the one shown in FIG. 2, a distal portion of the tubing 120 is expandable, permitting suction to be applied over a larger area while minimizing the diameter of tubing that must be passed through the sheath. This may be implemented by varying the wall thickness of the distal portion of the tubing, incorporating one or more folds in the distal wall (not shown) and/or incorporating one or more structural elements (e.g. spines, rings or coils) into the wall of the distal portion of the tubing 120 to urge the distal portion of the wall of the tubing 120 outward. Alternatively, as shown in FIG. 4, the distal portion of the tubing 120 may have a substantially constant diameter and may not flare or otherwise expand when disposed in the renal pelvis or other body lumen.

When the scope or catheter 110 is attached to a distal portion of the tubing 120, such as in FIG. 1, the connection may be made by means of one or more clips, or by the use of an end-cap that is fixedly attached to the tubing 120 and is attachable to the scope or catheter 110. The scope or catheter 110 can be attached to the tubing 120 along the full length of the scope/catheter 110 or tubing 120, along a portion of the length, or even at a single point. Generally, the smaller the extent of the connection between the scope or catheter 110 and the tubing 120, the more freedom the two elements will have to move relative to one another. This can be advantageous in cases where the scope or catheter 110 and tubing 120 must be inserted through relatively tortuous anatomy, as the tubing 120 will be free to deform and move without impinging upon or potentially kinking the scope or catheter 110, though it may be desirable in some instances to utilize a connection along all or most of the length of the system, for example when suction or irrigation must be applied with high precision.

Figure 3:
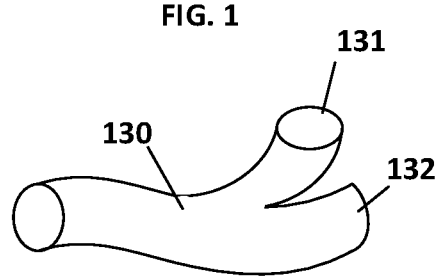
FIG. 3 shows a Y-junction at the proximal portion of a suction tube connectable to a suction source and including a port for insertion of a scope or other instrument.

Nesting the scope/catheter 110 within the tubing 120 is facilitated by the incorporation of a Y-connector 130 in the proximal portion of the tubing 120, as shown in FIG. 3. The Y connector will generally include a first port 131 connectable to an irrigation/suction source and a second port 132 into which the scope or catheter 110 is insertable. The ports 131, 132 preferably include fluid-tight connectors that are commonly used in the field, including luer connectors, barbed connectors, etc. In some cases, the connectors used in each port are distinct, to prevent mis-connection.

Because insertion of the PCNL sheath through the renal cortex may damage the kidney, it is desirable to minimize the outer diameter of the sheath and to maximize the use of its inner diameter. In a typical system according to the embodiments of FIGS. 1-4, the PCNL sheath may be 30 French (Fr) (10 mm in diameter) and the outer diameter of the tubing 120 may be 27 or 28 Fr (9-9.3 mm) The scope or catheter may be of any suitable diameter below 27 or 28 Fr. The PCNL sheath can be any size, for example, 3-34 French (Fr) and the outer diameter of the tubing 120 can be any size smaller than the size of the PCNL sheath. Additionally, because PCNL is typically performed under ultrasound or fluoroscopic guidance, the scope or catheter 110 and/or the tubing 120 optionally incorporate materials or features that are visible under ultrasound (e.g. bubbles, textured surfaces, and/or materials with varying absorptive, reflective or refractive characteristics) or fluoroscopy (e.g. radiopaque materials such as barium sulfate).

Turning next to FIGS. 5A-5B and 6A-6B, those of skill in the art will appreciate that approaches to access the renal pelvis, and particularly the upper pole of the renal pelvis are limited by patient anatomy and will vary from patient to patient depending on the positioning of the stone(s) to be resolved, the vascularization of the kidney and surrounding tissue, and the patient's ability to assume (or to be placed in) a supine or prone position during the procedure. It will also be appreciated that, in some cases, stones may be tightly positioned within the upper pole of the renal pelvis so to obstruct access to the renal pelvis by these approaches. In other words, in some cases, a stone may limit or prevent the movement of instruments within the renal pelvis sheath placement. There are currently no means for repositioning such stones or for threading instruments past these stones. To address this need, certain embodiments of the present disclosure utilize guidewires 200 with self-expanding distal tip structures 210 that can be threaded past a stone in a collapsed configuration, and which expand once positioned beyond the stone in the renal pelvis, thereby anchoring the guidewire 200 in place and facilitating insertion of instruments, including catheters and scopes, over the wire and past the stone. To facilitate passage of the guidewire 200 past the stone, in preferred embodiments the guidewire 200 is steerable and/or incorporates a deflectable or curved distal end (not shown). In addition, in some cases, the distal tip structures 210 can advantageously apply force to such stones, helping to dislodge them. Once the guidewire 200 has been passed into the pelvis and anchored, a rotating burr similar to the Rotablator™ rotational burr system commercialized by Boston Scientific Corporation (Marlborough, Mass.) can be passed over the guidewire 200 and brought into contact with the stone. Thereafter, the burr can be activated to remove the stone, or to create a passage into or through which instruments may be passed.

While any suitable self-expanding geometry can be selected for the self-expanding tip 210, in preferred embodiments such as those shown in FIGS. 5A-5B and 6A-6B, an umbrella-like arrangement utilizing multiple tines is employed. Such arrangements advantageously reduce the amount of rotation necessary to orient the self-expanding tip 210 correctly, potentially reducing procedure times.

Figures 7A, 7B:
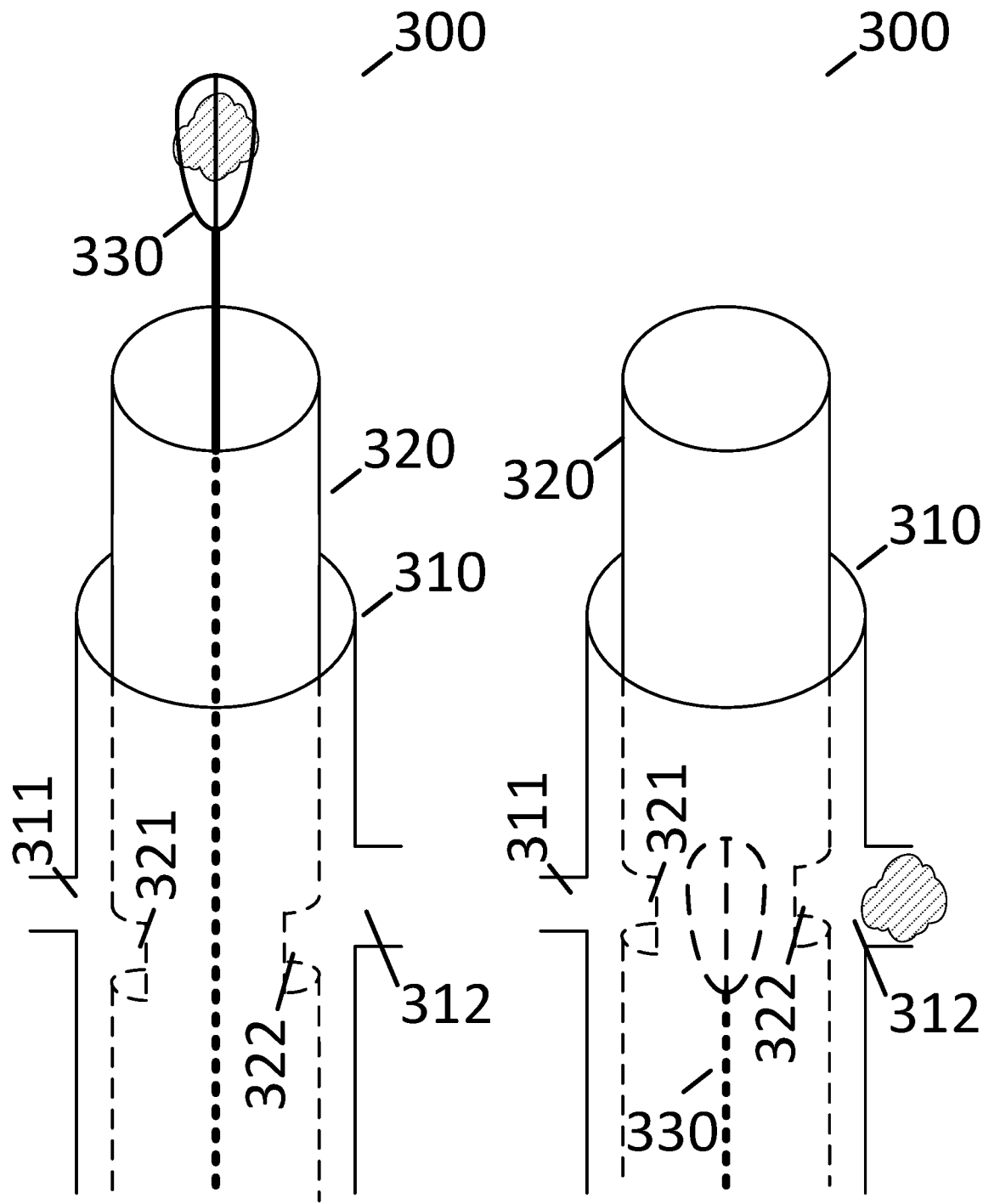
FIGS. 7A and 7B show two schematic views of an exemplary stone wash-out device.

Currently-available PCNL sheaths and systems require retraction and re-insertion of snare devices used to remove stones or stone fragments; these devices may be several feet in length, so removing them and reinserting them repeatedly during a procedure can add significant delay and complexity. In an exemplary PCNL system according to the present disclosure, as illustrated in FIGS. 7A-7B, stone removal is simplified by the introduction of a rapid stone exchange mechanism within the sheath. The system 300 includes an outer sheath 310 with first and second apertures 311, 312 made in opposite sidewalls of the outer sheath 310 and an inner sheath 320 slidably disposed within the outer sheath 310, which has first and second apertures 321, 322 in opposite sidewalls that are complementary to (i.e. can be aligned with) the first and second apertures 311, 312 of the outer sheath 310. An instrument such as a snare 330 can be inserted through and out of the inner sheath 320, (as shown in FIG. 7A) for instance to retrieve a stone or fragment thereof, then retracted into the inner sheath 320 (as shown in FIG. 7B) so that the stone or fragment is aligned with the first and second apertures 321, 322. This is optionally facilitated by the inclusion of one or more flanges or tabs (not shown) on an inner surface of the inner sheath 320 which can be sized to permit the empty snare 330 to slide into the sheath, while preventing retraction of the snare 330, when loaded with a captured stone or fragment, past the first and second apertures 321, 322 of the inner sheath 320. Once the snare 330 and stone are aligned with the first and second apertures 321, 322 of the inner sheath 320, they are moved within the outer sheath 310 to align the first and second apertures 311, 312. Once aligned, irrigation applied through the first aperture 311 and/or suction applied through the second aperture 312 of the outer sheath 310 urges the stone or fragment away from its point of engagement with the snare 310 and, optionally, into a trap (not shown) fluidly connected to the second aperture 312, where the stone or fragment can be retrieved, for example for pathology purposes.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present disclosure are described above. It is, however, expressly noted that the present disclosure is not limited to those embodiments, but rather the intention is that additions and modifications to what was expressly described herein are also included within the scope of the disclosure. Moreover, it is to be understood that the features of the various embodiments described herein were not mutually exclusive and can exist in various combinations and permutations, even if such combinations or permutations were not made express herein, without departing from the spirit and scope of the disclosure. In fact, variations, modifications, and other implementations of what was described herein will occur to those of ordinary skill in the art without departing from the spirit and the scope of the disclosure. As such, the disclosure is not to be defined only by the preceding illustrative description.

The invention claimed is:

1. A method for treating a patient, comprising the steps of:
inserting, into a renal pelvis of the patient and through an access sheath, a guidewire comprising a self-expanding distal-tip structure;
positioning the self-expanding distal-tip structure proximally to an object within the renal pelvis such that the self-expanding distal-tip structure assumes an expanded configuration;
altering a size or shape of the object by fragmenting the object, thereby forming a fragment of the object;
inserting a snare into the renal pelvis through the access sheath, the snare and the guidewire being independent of each other;
grasping the fragment of the object with the snare;
retracting the snare into the access sheath; and
engaging the fragment of the object with an aperture disposed in a sidewall of the access sheath by applying suction through the aperture.

2. The method of claim 1, wherein the guidewire is advanced through a working channel of a nephroscope, and at least a portion of the nephroscope is positioned within a catheter configured to apply suction or deliver fluid.

3. The method of claim 1, wherein the step of positioning the self-expanding distal-tip structure proximally to the object includes moving the object.

4. The method of claim 2, wherein the nephroscope is attached to a wall of the catheter configured to apply suction.

5. The method of claim 1, further comprising passing a burring instrument over the guidewire so as to contact the object; and activating the burring instrument, thereby altering the size or shape of the object.

* * * * *